(12) United States Patent
Mikalsen

(10) Patent No.: US 10,793,487 B2
(45) Date of Patent: Oct. 6, 2020

(54) PROCESS FOR PRODUCING METHANOL AND/OR METHANE

(71) Applicant: Terje Ernst Mikalsen, Østerås (NO)

(72) Inventor: Terje Ernst Mikalsen, Østerås (NO)

( * ) Notice: Subject to any disclaimer, the term of this patent is extended or adjusted under 35 U.S.C. 154(b) by 0 days.

(21) Appl. No.: 16/341,750

(22) PCT Filed: Oct. 13, 2017

(86) PCT No.: PCT/NO2017/050264
§ 371 (c)(1),
(2) Date: Apr. 12, 2019

(87) PCT Pub. No.: WO2018/070878
PCT Pub. Date: Apr. 19, 2018

(65) Prior Publication Data
US 2020/0048159 A1 Feb. 13, 2020

(30) Foreign Application Priority Data

Oct. 13, 2016 (NO) .................................. 20161640

(51) Int. Cl.
*C07C 1/12* (2006.01)
*A01K 61/60* (2017.01)
(Continued)

(52) U.S. Cl.
CPC ................ *C07C 1/12* (2013.01); *A01K 61/10* (2017.01); *A01K 61/50* (2017.01); *A01K 61/60* (2017.01);
(Continued)

(58) Field of Classification Search
CPC ......... C07C 1/12; C07C 29/1518; C07C 9/04; C07C 31/04; C25B 1/04; A01K 61/10; A01K 61/50; A01K 61/60
See application file for complete search history.

(56) References Cited

U.S. PATENT DOCUMENTS

2013/0112151 A1    5/2013   Mizrachi

FOREIGN PATENT DOCUMENTS

DE    4332789 A1    3/1995
EP    2978732 B1    2/2016
(Continued)

OTHER PUBLICATIONS

International Search Report in International Application No. PCT/NO2017/050264 dated Jan. 9, 2018.
(Continued)

*Primary Examiner* — Rosalynd A Keys
(74) *Attorney, Agent, or Firm* — Greenberg Traurig, LLP; David J. Dykeman; Natalie Salem

(57) ABSTRACT

It is disclosed a system for producing methanol/methane, said system comprising an electrolysis section (1) producing hydrogen and oxygen from the cleaving of water molecules, and said system further comprising a closed cultivation/breeding container/pond (5) for aquatic organisms creating $CO_2$ through their metabolism to be liberated into the water surrounding said organisms forming $CO_2$-rich water, said $CO_2$-rich water being transported to a $CO_2$-liberating section forming gaseous $CO_2$ and $CO_2$-poor water, said liberated gaseous $CO_2$ being transported to a reactor (6,6') and being combined with said hydrogen from said electrolysis plant (1) for creating methanol and/or methane as an end product, said methanol/methane being isolated and exited from said system.

15 Claims, 1 Drawing Sheet

(51) Int. Cl.
*A01K 61/10* (2017.01)
*C07C 29/151* (2006.01)
*C25B 1/04* (2006.01)
*C07C 9/04* (2006.01)
*A01K 61/50* (2017.01)

(52) U.S. Cl.
CPC ............ *C07C 29/1518* (2013.01); *C25B 1/04* (2013.01); *C07C 9/04* (2013.01)

(56) References Cited

FOREIGN PATENT DOCUMENTS

| JP | 2003259759 A | 9/2003 |
|----|--------------|--------|
| WO | 1995021423 A1 | 8/1995 |
| WO | 1996036219 A1 | 11/1996 |

OTHER PUBLICATIONS

International Preliminary Report on Patentability in International Application No. PCT/NO2017/05026 dated Sep. 6, 2018.
Norwegian Search Report in Norwegian Patent Application No. 20161640 dated May 2, 2017.

PROCESS FOR PRODUCING METHANOL AND/OR METHANE

CROSS-REFERENCE AND CLAIM OF PRIORITY TO RELATED APPLICATIONS

This application is a U.S. national phase application under 35 U.S.C. 371 of International Patent Application No. PCT/NO2017/050264, filed on Oct. 13, 2017, which claims the benefit of and priority to Norwegian patent application no. 20161640, filed Oct. 13, 2016, each of which are hereby incorporated by reference in their entireties.

BACKGROUND

Based on both environmental and economic considerations it is advantageous to use $CO_2$ being dissolved or stored in water. The combination of farming aquatic animals such as fish for creating carbon dioxide dissolved in the water from the fish farming plant, removing the carbon dioxide from the breeding water and combining this sequestered carbon dioxide with hydrogen for creating compounds for further exploitation, such as methanol and/or methane, will not only provide a sustainable living environment for the aquatic animals by removing said carbon dioxide, but will also provide a source for carbon dioxide to be used as starting materials for producing methane and/or methanol. The produced methanol/methane may be further used for producing e.g. fish feed. A combination of fish breeding with the production of methanol/methane will improve both processes to be more environmentally friendly and sustainable.

PRIOR ART

The production of methanol through a reaction of carbon dioxide and hydrogen is known from WO 95/214123. Hydrogen gas and oxygen gas is produced through electrolysis of water. The oxygen gas is then introduced into a carbon-based process wherein $CO_2$ is produced as a waste gas. The $CO_2$ gas is subsequently isolated and transported to a methanol-generating unit. In this unit hydrogen gas is added and methanol is produced by a reaction between the hydrogen and the carbon dioxide. Instead of the $CO_2$ gas being treated as a waste product this is being used for producing methanol.

A process for producing methanol is also known from DE patent 4332789 through a reaction between carbon dioxide and hydrogen, wherein the hydrogen originates from the hydrolysis of water. A similar process is known from EP 2978732 B1 disclosing a method for producing methane wherein hydrogen originating from the hydrolysis of water is reacted with $CO_2$ in a reactor for producing methane.

For cultivating and breeding aquatic organisms it is generally known that $CO_2$ should be removed from the water and that the water should be added oxygen for sustaining the living conditions for the aquatic animals. This is e.g. disclosed in US 2013/0112151 A1. JP 2003259759 A discloses removing carbon dioxide from an aqua culture plant while supplying oxygen.

BRIEF SUMMARY

The present invention relates to a process for producing methanol and/or methane by using carbon dioxide sequestered from dissolved carbon dioxide in water taken or isolated from a land-based plant for raising or farming aquatic animals such as fish combined with hydrogen originating from electrolysis of water through the reactions (I) or (II)

$$CO_2 + 3H_2 => CH_3OH + H_2O \quad (I)$$

$$CO_2 + 4H_2 => CH_4 + 2H_2O \quad (II)$$

wherein the methanol/methane is created through the steps of a) electrolysis of water for forming hydrogen gas and oxygen gas, b) transferring the oxygen gas from step a) to a plant for breeding aquatic animals for oxygenating the water in said plant to be used for the animal's breathing of the water in said plant for forming $CO_2$ to be sequestered from said breeding water to be used in the reactions (I) or (II) supra, and c) returning said sequestered carbon dioxide to a plant for conducting the reaction(s) (I) and/or (II) supra for creating methanol and/or methane by combining said carbon dioxide with the hydrogen originating from said electrolysis of water. Particularly the present invention is related to the use of carbon dioxide-rich water from a land-based breeding plant for aquatic animals, e.g. fish farms, for rich water from a land-based breeding plant for aquatic animals, e.g. fish farms, for producing methanol and/or methane by combining said carbon dioxide with hydrogen originating from electrolysis of water and further optionally returning the by-product oxygen originating from said electrolysis of the water to the water in the breeding plant for said aquatic animals.

DETAILED DESCRIPTION

1a. Production of Methanol

Figure 1:
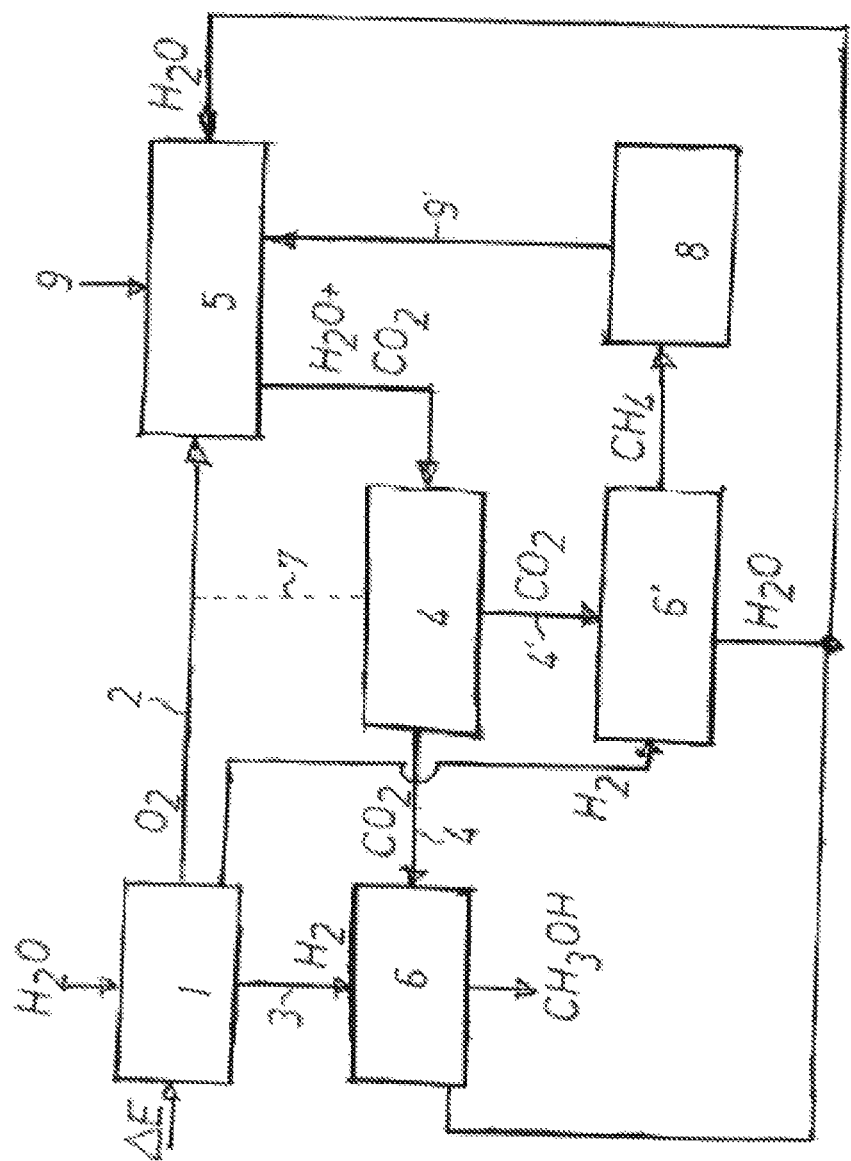
FIG. 1 depicts a flow chart for a system for producing methanol/methane according to the invention, wherein said system includes an electrolysis section 1 producing hydrogen and oxygen from the cleaving of water molecules, and said system further including a closed cultivation/breeding container/pond 5 for aquatic organisms creating CO2 to be liberated into the water surrounding said organisms forming CO2-rich water, said CO2-rich water being transported to a CO2-liberating section 4 forming gaseous CO2 and CO2-poor water, said liberated gaseous CO2 being transported to a reactor 6,6' and being combined with said hydrogen from said electrolysis plant 1 for creating methanol and/or methane as an end product, said methanol/methane being isolated and exited from said system. The methane may be supplied to a bacterial culture 8 as a growth substrate for creating protein to be used in e.g. fish feed.

Based on a newly developed technology by "Carbon Recycling International" (CRI), 201 Kopavogur, Iceland (www.CRI.IS) methanol may be produced in an industrial scale from $CO_2$ and $H_2$.

$$CO_2 + 3H_2 => CH_3OH + H_2O$$

When the hydrogen gas is produced through electrolysis of water or through natural gas by renewable energy such as by energy issued from solar panels, wind power plants/windmills or conventional water power plants, methanol as well as other products that may be produced based on methanol, may be said to be "green" or environmentally friendly (i.e. without or with a small environmental load)

and ranges from additives for fuels to glue in fiber wood as well as plastics in tools, toys, cars or accessories such as kitchen equipment, aids for the handicapped, rails, etc.

The electrolysis of water creates oxygen gas as well in an amount of about 8 kg oxygen per kilogram of hydrogen gas, as well as hot water from the cooling of the electrolysis plant, where both these items are wanted for a land-based plant for cultivating or breeding aquatic organisms such as in fish cultivation plants.

1b. Production of Methane

Methane may be produced from $CO_2$ and $H_2$ via a Sabatier-reactor producing methane through the overall reaction $$CO_2 + 4H_2 => CH_4 + 2H_2O$$

In this reaction it is additionally produced heat. The methane gas is fed into a recently developed fermenting reactor (developed by "Bioferm/Calysta") producing fish feed ("FeedKind"™ protein) as a replacement for fish meal being supplied to the fish.

The electrolysis of water forming oxygen and hydrogen, may be included in a closed circuit being connected to a conduit for supplying isolated $CO_2$ originating from the combustion of oxygen by fish through their metabolism (dissolved in the water or supplied externally) and carbon through the fish feed, wherein $CO_2$ dissolved in the water may be sequestered by using state of the art techniques such as membrane extraction, aeration through pressure reduction, by using ultrasound waves for forming $CO_2$ bubbles, etc.

The isolated carbon dioxide may be thus be connected to both the production of methanol and/or methane in a closed circuit whereon $O_2$ is formed by the electrolysis of water being transported in a closed circuit to a fish farming plant that subsequently produces carbon dioxide that may be used for producing methanol and/or methane as explained supra. The methane may subsequently be used as a raw material for the production of e.g. fish feed that may be fed back to the fish as well.

Thus the present invention concerns, in one embodiment, the use of $CO_2$ extracted/sequestered from water from an aqua-farming plant such as a land-based fish-farming plant for producing methanol/methane through adding hydrogen to said $CO_2$ and reacting said hydrogen with said carbon dioxide in agreement with the above reactions (I) and/or (II). The produced methanol/methane may be used as starting materials for further production of articles. In one embodiment the sequestration of $CO_2$ may be accomplished by the water in the cultivation/breeding tank being circulated in a closed system to a unit liberating $CO_2$ from the water. It has not been found that capturing $CO_2$ from water originating from the cultivation of aqueous organisms has been suggested as a starting material for the production of methanol and/or methane or that this has been attempted before. The system provides a unique circular supply chain and it is self-sufficient, as detailed below, since the fish provide enough $CO_2$ to feed a methanol/methane and hydrolyzer plant that in turn will provide more oxygen as a bi-product than needed by the fish.

The expression "fish farming plant" or "plant for farming aquatic animals" should in the present context be interpreted to include the farming or breeding of other aquatic animals besides fish, e.g. crustaceans (crayfish, shrimp, crab) or mollusks (oysters, scallops, etc.). A fish farming plant may include a fresh water plant as well as a salt water plant provided they are closed systems and are not to any significant extent supplied with water from external sources. Such a combination of electrolysis of water and the production of $CO_2$ from aquatic animals will also qualify as a carbon-negative process with an advantageous effect on the climate and particularly the water quality in the fish breeding plant. The combined plants will produce fish with no or insignificant outlet to the environment and also bio-based methanol/methane, all provided the electric power used is taken from a renewable source.

It is well known to make bio-fuels like bio-ethanol from plants and trees, but it is also a well-known concern that demand for such fuels might lead to overtaxing of the bio-production capacity in nature and start competing with food production. In the case of the present invention, more demand for bio-fuel will stimulate more production of fish.

2. Fish Farming in Closed and Land-Based Plants with Return of Water

In a closed system it is possible to obtain optimal growth and breeding conditions for the aquatic organisms/fish and additionally avoid serious diseases or environmental problems including diseases/fish diseases and the escaping of fish because the water is returned to the fish farming plant subsequent to purification/filtration/sedimentation/flotation and temperature adjustment. However, it is required a lot of $O_2$ to spruce up the water (the fish using oxygen dissolved in the water for their energy/metabolism while producing $CO_2$ through such metabolism). In a closed cultivation system it is also possible to cultivate other organisms such as crustaceans (crawfish etc.) and scallops (fresh water scallops) being organisms that require oxygen for their metabolism as well.

The electrolysis plant will, through the electrolysis of water, provide the required $H_2$ to the methanol/methane production as well as $O_2$ together with hot water that may be used for:
 more convenient extraction of $CO_2$ from the water in the fish farming ponds,
 the treatment of sediments and waste and storage thereof to useful biomass,
 regulating the temperature in the raising and breeding ponds/tanks,
 supplying hot water for slaughtering the fish, sanitizing equipment, sanitary treatment of the fish meat, etc.

Hot water may in one embodiment also be used in heat exchanger for elevating the temperature of the water from the fish cultivation tank(s) for preparing removal of the entrained $CO_2$ therein. Cold water is known to assimilate gases such as $O_2$ and $CO_2$ better than hot water. E.g. water at a temperature of 60-90° C. carries far less entrained gas than water at e.g. 4-15° C. Consequently the temperature in the fish cultivation and breeding tanks is maintained at temperatures that are suitable for the aquatic animals therein. $CO_2$-rich water from the cultivation/breeding tank(s) will in one embodiment consequently be heated after having been removed from the cultivation tank(s) but prior to the $CO_2$ removal step of the process according to the invention.

Extraction of $CO_2$ from water is known inter alia from "SFE Extraction and $CO_2$ Extraction" (www.waters.com).

For each molecule of $O_2$ being used by the aqueous organisms/fish, said organisms/fish forms one molecule of $CO_2$, or per weight:
 1000 kg $O_2$ => 1200 kg $CO_2$ giving a $CO_2$-factor of 1, 2.

In a closed system carrying live aqueous organisms $CO_2$ has to be removed from the water for maintaining acceptable living conditions for the organisms such as acceptable pH-values (normally about pH 6-8, preferably about pH 7). $CO_2$ is normally associated with elevating the pH of water by forming carbonic acid ($CO_2 + H_2O => H_2CO_3$), and is considered to be a waste product with negative environmental consequences. Many of such negative consequences are dealt with in closed systems such as the system according to the present invention.

The present invention will become better understood with reference to the FIG. 1 showing an embodiment of a system according to the present invention combining the formation of oxygen 2 and hydrogen 3 from electrolysis 1 of water wherein $CO_2$ is isolated 4,4' from the water taken from used water including entrained $CO_2$ from a cultivation/breeding tank/pond 5 for aquatic animals/fish. The isolated $CO_2$ is reacted with hydrogen originating from the electrolysis 1 of water forming methane and/or methanol 6,6' as explained supra. In one embodiment the methane may be supplied to a bacterial culture 8 as a growth substrate for creating protein to be used in e.g. fish feed. Such protein may in one embodiment constitute about 30% of protein included in such fish feed.

In an alternative embodiment methanol created by the process according to the invention may be used as a starting material for making more complex substances (e.g. plastics, oil, etc.) or may be used as a fuel or a fuel additive.

In one embodiment hot water used in the system according to the invention may be supplied from an external source or may be water recirculated from the cultivation/breeding tank 5. In an alternative the $CO_2$-poor water from the carbon dioxide-extracting section 4 may be supplied with oxygen 2 originating from the electrolysis section 1 of the system according to the invention and be returned in an oxygen-rich state back to the cultivation/breeding tank/pond 5. This is indicated by a dotted line 7 running from the carbon dioxide removal stage 4 to the supply line 2 carrying oxygen from the electrolysis stage 1 to the cultivation/breeding tank/pond 5.

The energy in the hot water from the electrolysis stage 1 may be heat-exchanged into cooling of the water in closed plants (not shown). Hot water (exceeding 80° C.) being collected as a by-product from the production stages of methanol and methane 6,6', may be used for disinfection or directly for slaughtering fish, and may additionally and optionally be used for drying sludge collected from the cultivation/breeding tank/pond 5. Such sludge may in one embodiment be used as e.g. fertilizer.

In a closed cultivation system for aquatic animals/fish excess $CO_2$ should be removed from the water for maintaining acceptable pH values, and the $CO_2$ is also considered as a waste product with negative environmental effects such as e.g. acidification of the water through the formation of $H_2CO_3$ and $HCO_3$. A too high content of $CO_2$ in the water will also have as a consequence that it will become difficult for the aquatic animals to "breathe" (the water becomes $CO_2$-poisoned). Several other environmental consequences, e.g. the prevention and/or treatment of diseases and parasites (e.g. salmon lice), escape, no effect on the environment through medication, removal of waste (feces, dead animals, over-feeding, etc.) is easily taken care of in closed cultivation/breeding systems.

Regular feed or feed/protein produced from the bacterial fermentation of $CH_4$ in the fermentor 8 may be introduced into the fish farming tank/pond 5 through lines 9,9'.

3. The addition of extra oxygen ($O_2$) to fish cultivation/breeding/farming plants has been recommended in studies performed by IRIS (previously Rogalands-forskning), but integration with a methanol or methane production plant is a new concept. The new concept is to capture $CO_2$ created by cultivated/bred organisms/fish and process this as a raw material in the methanol/methane plant. This idea is new probably because the technology for producing methanol, as disclosed supra, is rather new. The use of $CO_2$ in this way reduced the capital expenses with about 30% and the production costs with about 14% for the methanol production and free oxygen and heat assists in making land-based fish raising and breeding plants very profitable. By utilizing $CO_2$ for producing methane and fish feed about 30% of the expenses may be saved for necessary feed.

The liberated oxygen expelled from the electrolysis plant 1 may also be used for other purposes than the addition to a fish cultivation/breeding plant, e.g. for combustion systems/plants for garbage, from which further $CO_2$ may be introduced into the methanol/methane production plant 6,6' (not shown).

The balance for the methanol production related to fish farming/breeding (per 1000 kg methanol) is:
produced $O_2$ from $H_2O$: 1541 kg
75% of $O_2$ introduced in the fish farming: 1157 kg
$CO_2$ available from the fish: 1157·1, 2=1388 kg
$CO_2$ required for producing methanol: 1380 kg≈balance Some extra oxygen may be provided to the fish because the fish may not be able to assimilate it all. The extra oxygen originating from the electrolysis covers this requirement.

FIG. 1 depicts a possible flow chart for a system for producing methanol/methane according to the invention, wherein said system includes an electrolysis section 1 producing hydrogen and oxygen from the cleaving of water molecules, and said system further including a closed cultivation/breeding container/pond 5 for aquatic organisms creating $CO_2$ to be liberated into the water surrounding said organisms forming $CO_2$-rich water, said $CO_2$-rich water being transported to a $CO_2$-liberating section forming gaseous $CO_2$ and $CO_2$-poor water, said liberated gaseous $CO_2$ being transported to a reactor 6,6' and being combined with said hydrogen from said electrolysis plant 1 for creating methanol and/or methane as an end product, said methanol/methane being isolated and exited from said system.

Technology for harvesting $CO_2$ from water in an industrial scale is available as explained supra, and the system according to the invention will, in one embodiment, capture the formed $CO_2$ as well and thereby avoid accumulation. If this security measure should fail, there exist methods for removing $CO_2$ from water without capturing the $CO_2$, e.g. like bubbling air through the water in an aquarium.

The loops for transporting oxygen, hydrogen and carbon dioxide between a methanol/methane production plant and a plant for cultivating/breeding aquatic organisms/fish improve both to a large extent by:
1. Reducing both capital and production expenses for the methanol/methane production.
2. Providing a continuous supply of oxygen and energy to the fish raising/breeding plant.
3. Replacing parts of the need for fish feed.

In summary the present invention may be presented by the following features:

The process according to the invention is conducted by producing methanol and/or methane by the reactions (I) and/or (II)

$$CO_2+3H_2 => CH_3OH+H_2O \qquad (I)$$

$$CO_2+4H_2 => CH_4+2H_2O \qquad (II)$$

wherein the methanol/methane is created through the steps
a) electrolysis of water for forming hydrogen gas and oxygen gas,
b) transferring the oxygen gas from step a) to a plant for breeding aquatic animals for oxygenating the water in said plant to be used for the animal's breathing of the water in said plant for forming $CO_2$ to be sequestered from said cultivation/breeding water to be used in the reactions (I) or (II) supra, and c) returning said sequestered carbon dioxide to a plant for conducting the reaction(s) (I) and/or (II) supra for creating methanol and/or methane by combining said carbon dioxide with the hydrogen originating from said electrolysis of water.

Alternatively the invention may be viewed as using carbon dioxide-rich water originating from a cultivation plant/container/pond for aquatic animals/fish, after the liberation of said carbon dioxide from said cultivation/breeding water, to be combined with hydrogen originating from electrolysis of water for forming methanol and/or methane.

The aquatic animals such as fish that may be cultivated/bred in a closed cultivation/breeding plant comprises fish types such as e.g. carp, mullet, bass, abbor, pike, trout, etc. The water used for cultivating/breeding the aquatic animals may be salt or fresh, fresh water being preferred. Organisms thriving in fresh water other than fish, and that may be cultivated in a land-based closed cultivation/breeding plant either alone or together with the different fish types, may be fresh water crawfish, fresh water clams, pearl fresh water oysters, etc.

The invention claimed is:

1. A system for producing methanol/methane, said system comprising:
    an electrolysis stage (1) configured to produce hydrogen and oxygen from the cleaving of water molecules; and
    a closed cultivation/breeding plant (5) for aquatic organisms creating $CO_2$ through the metabolism of the aquatic organisms and through biodegradation of faeces and unused feed at the bottom of the breeding/cultivation plant to be liberated into the water surrounding said organisms forming $CO_2$-rich water, wherein said system is configured to transport $CO_2$-rich water to a $CO_2$-liberating section (4) forming gaseous $CO_2$ and $CO_2$-poor water (7),
    wherein said system is configured to transport said liberated gaseous $CO_2$ to a reactor (6,6') for reaction with said hydrogen from said electrolysis stage (1) for producing methanol and/or methane as an end product, said methanol/methane being isolated and exited from said system,
    wherein said system is configured to introduce the oxygen liberated from said cleaving of water molecules into the water in the cultivation/breeding plant (5).

2. The system according to claim 1, wherein said oxygen is added to the $CO_2$-poor water originating from said $CO_2$-liberating section (4) prior to its re-introduction to the cultivation/breeding plant (5).

3. A process for producing methanol/methane by the use of a system according to claim 1, wherein the methanol and/or methane is formed through the overall reactions

$$CO_2 + 3H_2 => CH_3OH + H_2O \quad (I)$$

$$CO_2 + 4H_2 => CH_4 + 2H_2O \quad (II)$$

wherein the methanol/methane is produced through the steps of:
a) electrolysis of water for forming hydrogen gas and oxygen gas,
b) isolating carbon dioxide ($CO_2$) from the $CO_2$-rich water originating from aquatic organisms' breathing of the water in said plant for forming $CO_2$ to be sequestered from said water to be used in the reactions (I) or (II) supra, and
c) returning said sequestered carbon dioxide to a plant for conducting the reaction(s) (I) and/or (II) supra for creating methanol and/or methane by combining said carbon dioxide with the hydrogen originating from said electrolysis of water,
wherein the oxygen liberated from the electrolysis of the water is introduced into the water in the cultivation/breeding plant (5) for the aquatic organisms.

4. The process according to claim 3 wherein carbon dioxide-rich water from a land-based breeding plant for aquatic organisms is used for producing methanol and/or methane by combining said carbon dioxide with hydrogen originating from electrolysis of water and returning the oxygen originating from said electrolysis of the water to the water in the breeding plant for said aquatic organisms.

5. The process according to claim 3, wherein said cultivating/breeding plant (5) is a closed fish farming plant wherein the water is re-circulated after having been liberated of $CO_2$.

6. The process according to claim 3, wherein hot water originating from the electrolysis of water is supplied to the cultivation/breeding plant to be used in disinfection or slaughtering of edible aquatic animals and/or controlling the temperature in the breeding/cultivating plant.

7. The process according to claim 3, wherein the aquatic organisms are fishes raised in a land-based cultivation/breeding plant.

8. The use of $CO_2$-rich water originating from a plant for cultivating/breeding aquatic organisms comprising isolating $CO_2$ and reacting the $CO_2$ with hydrogen originating from the electrolysis of water for forming methanol and/or methane in a process according to claim 3.

9. The process according to claim 3 further utilizing the produced methane and/or methanol for producing fish feed.

10. The process according to claim 4 wherein the land-based breeding plant for aquatic organisms are fish farms.

11. The process according to claim 3 wherein said aquatic organisms are different from fish.

12. The process according to claim 7 wherein the fishes are one or more of carp, mullet, bass, pike, abbor and trout.

13. The process according to claim 11 wherein the aquatic organisms are crustaceans or mollusks.

14. The process according to claim 11 wherein the aquatic organisms are one or more of fresh water crayfish, fresh water pearl clams, and fresh water scallops.

15. The use according to claim 8 comprising producing fish feed from the methane and/or methanol.

* * * * *